US005453492A

United States Patent [19]
Bützow et al.

[11] Patent Number: 5,453,492
[45] Date of Patent: Sep. 26, 1995

[54] 60 KDA TRANSFORMING GROWTH FACTOR-β-BINDING PROTEIN AND ITS USE TO DETECT OR PURIFY TGF-β

[75] Inventors: Ralf Bützow, Helsinki, Finland; Erkki Ruoslahti, Rancho Santa Fe, Calif.

[73] Assignee: La Jolla Cancer Research Foundation, La Jolla, Calif.

[21] Appl. No.: 98,647

[22] Filed: Jul. 28, 1993

[51] Int. Cl.[6] .......................... C07K 14/435; C07K 1/22; G01N 33/58
[52] U.S. Cl. .......................... 530/413; 530/350; 530/395; 530/402; 435/7.1
[58] Field of Search .................................. 530/350, 351, 530/395, 413, 402; 514/1, 8; 435/7.1

[56] References Cited

U.S. PATENT DOCUMENTS 5,229,495  7/1993  Ichijo et al. .................. 530/350

FOREIGN PATENT DOCUMENTS

WO90/00194  1/1990  WIPO.
WO91/04748  4/1991  WIPO.
WO91/10727  7/1991  WIPO.
WO93/10215  5/1993  WIPO.
WO93/10808  6/1993  WIPO.

OTHER PUBLICATIONS

Miller et al., "Characterization of the Binding of Transforming Growth Factor-β1, -β2, and -β3 to Recombinant β1-Latency-Associated Peptide" *Mol. Endoc.* 6:694–702 (1992).
Murphy-Ullrich et al., "Transforming Growth Factor-β Complexes with Thrombospondin" *Mol. Biol. Cell* 3:181–188 (1992).
Paralkar et al., "Transforming Growth Factor β Type 1 Binds to collagen IV of Basement Membrane Matrix: Implications for Development" *Dev. Biol.* 143:303–308 (1991).
Pearson et al., "Tenascin: cDNA cloning and induction by TGF-β" *EMBO J.* 7:2977–2981 (1988).
Gougos and Letarte, "Identification of a Human Endothelial Cell Antigen With Monoclonal Antibody 44g4 Produced Against a Pre–B Leukemic Cell Line" *J. Immun.* 141:1925–1933 (1988).
O'Connell et al., "Endoglin: a 180–kD endothelial cell and macrophage restricted differentiation molecule" *clin. exp. Immunol.* 90:154–159 (1992).
Gougos and Letarte, "Biochemical characterization of the 44G4 Antigen from the HOON Pre–B Leukemic Cell Line" *J. Immunol.* 141:1934–1940 (1988).
Quackenbush et al., "Differential Localization within Human Kidney of Five Membrane Proteins Expressed on Acute Lymphoblastic Leukemia Cells" *J. Immunol.* 136:118–124 (1986).
Quackenbush and Letarte, "Identification of Several Cell Surface Proteins of Non–T, Non–B Acute Lymphoblastic Leukemia by Using Monoclonal Antibodies" *J. Immunol.* 134:1276–1285 (1985).
Andres et al., "Membrane–anchored and Soluble Forms of Betaglycan, a Polymorphis Proteoglycan that Binds Transforming Growth Factor–β" *J. Cell Biol.* 109:3137–3145 (1989).
Balza et al., "Transforming growth factor β regulates the levels of different fibronectin isoforms in normal human cultured fibroblasts" *FEBS Letters* 228:42–44 (1988).
Bassols and Massague, "Transforming Growth Factor β Regulates the Expression and Structure of Extracellular Matrix Chondroitin/Dermatan Sulfate Proteoglycans" *J. Biol. Chem.* 263:3039–3045 (1988).
Bodmer et al., "Transforming Growth Factor–Beta Bound to Soluble Derivatives of the Beta Amyloid Precursor Protein of Alzheimer's Disease" *Biochem. Biophys. Res. Comm.* 171:890–897 (1990).

(List continued on next page.)

*Primary Examiner*—Garnette D. Draper
*Assistant Examiner*—David L. Fitzgerald
*Attorney, Agent, or Firm*—Campbell and Flores

[57] ABSTRACT

This invention provides a novel purified TGF-β binding protein, alone or complexed with TGF-β. The TGF-β binding protein is useful to purify TGF-β in a sample and to modify the regulatory activities of TGF-β.

5 Claims, 6 Drawing Sheets

OTHER PUBLICATIONS

Border et al., "Natural inhibitor of transforming growth factor–β protects against scarring in experimental kidney disease" *Nature* 360:361–364 (1992).

Border et al., "Transforming Growth Factor–β in Disease: The Dark side of Tissue Repair" *J. Clin. Invest.* 90:1–7 (1992).

Cheifetz et al., "Endoglin Is a Component of the Tranforming Growth Factor–β Receptor System in Human Endothelial Cells" *J. Biol. Chem.* 267:19027–19030 (1992).

Cheifetz et al., "A Surface Component on GH3 Pituitary Cells That Recognizes Transforming Growth Factor–β, Activin, and Inhibit" *J. Biol. Chem.* 263:17225–17228 (1988).

Fava and McClure, "Fibronectin–Associated Transforming Growth Factor" *J. Cell. Physiol.* 131:184–189 (1987).

Flanders et al., "Transforming Growth Factor–β1: Histochemical Localization with Antibodies to Different Epitopes" *J. Cell Biol.* 108:653–660 (1989).

Fisher et al., "Purification and Partial Characterization of Small Proteoglycans I and II, Bone Sialoproteins I and II, and Osteonectin from the Mineral Compartment of Developing Human Bone" *J. Biol. Chem.* 262:9702–9708 (1987).

Gentry et al., "Type 1 Transforming Growth Factor Beta: Amplified Expression and Secretion of Mature and Precursor Polypeptides in Chinese Hamster Ovary Cells" *Mol. Cell. Biol.* 7:3418–3427 (1987).

Heine et al., "Colocalization of TGF–beta 1 and collagen I and III, fibronectin and glycosaminoglycans during lung branching morphogenesis" *Development* 109:29–36 (1990).

Ignotz and Massague, "Cell Adhesion Protein Receptors as Targets for Transforming Growth Factor–β Action" *Cell* 51:189–197 (1987).

Ignotz and Massague, "Transforming Growth Factor–β Stimulates the Expression of Fibronectin and Collagen and Their Incorporation into the Extracellular Matrix" *J. Biol. Chem.* 261:4337–4345 (1986).

Kim et al., "Promoter Sequences of the Human Transforming Growth Factor–β1 Responsive to Transforming Growth Factor–β1 Autoinduction" *J. Biol. Chem.* 264:7041–7045 (1989).

Knabbe et al., "Evidence That Transforming Growth Factor–β Is a Hormonally Regulated Negative Growth Factor in Human Breast Cancer Cells" *Cell* 48:417–428 (1987).

Laemmli, "Cleavage of Structural Proteins during the Assembly of the Head of Bacteriophage T4" *Nature* 227:680–685 (1970).

Laiho et al., "Transforming Growth Factor–β Induction of Type–1 Plasminogen Activator Inhibitor" *J. Biol. Chem.* 262:17467–17474 (1987).

Leavitt et al., "Expression of Transfected Mutant β–Actin Genes: Alterations of Cell Morphology and Evidence for Autoregulation in Actin Pools" *Mol. Cell. Biol.* 7:2457–2466 (1987).

Lin et al., "Expression Cloning of the TGF–β Type II Receptor, a Functional Transmembrane Serine/Threonine Kinase" *Cell* 68:775–785 (1992).

McCaffrey et al., "Transfroming Growth Factor–β1 Is a Heparin–Binding Protein: Indentification of Putative Heparin–Binding Regions and Isolation of Heparins With Varying Affinity for TGF–β1" *J. Cell. Physiol.* 152:430–440 (1992).

Massague, "Subunit Structure of a High–affinity Receptor for Type β–transforming Growth Factor" *J. Biol. Chem.* 260:7059–7066 (1985).

Massague, "The Transforming Growth Factor–β Family" *Ann. Rev. Cell Biol.* 6:597–641 (1990).

Massague, "Receptors for the TGF–β Family" *Cell* 69:1067–1070 (1992).

Masui et al., "Type β transforming growth factor is the primary differentiation–inducing serum factor for normal human brochial epithelial cells" *Proc. Natl. Acad. Sci. USA* 83:2438–2442 (1986).

Nakamura et al., "Follistatin, an Activin–binding Protein, Associates with Heparan Sulfate Chains for Proteoglycans on Follicular Granulosa Cells" *J. Biol. Chem.* 266:19432–19437 (1991).

O'Connor–McCourt and Wakefield, "Latent Transforming Growth Factor–β in Serum" *J. Biol. Chem.* 262:14090–14099 (1987).

Roberts et al., "Transforming growth factor type β: Rapid induction of fibrosis and angiogenesis in vivo and stimulation of collagen formation in vitro" *Proc. Natl. Acad. Sci. USA* 83:4167–4171 (1986).

Ruoslahti and Yamaguchi, "Proteoglycans and Modulators of Growth Factor Activities" *Cell* 64:867–869 (1991).

Ruoslahti, "Structure and Biology of Proteoglycans" *Ann. Rev. Cell Biol.* 4:229–225 (1988).

Shipley et al., "Reversible Inhibition of Normal Human Prokeratinocyte Proliferation by Type β Transforming Growth Factor–Growth Inhibitor in Serum–free Medium" *Cancer Res.* 46:2068–2071 (1986).

Shull et al., "Targeted disruption of the mouse transforming growth factor–β1 gene results in multifocal inflammatory disease" *Nature* 359:693–699 (1992).

Silberstein et al., "Regulation of Mammary Morphogenesis: Evidence for Extracellular Matrix–Mediated Inhibition of Ductal Budding by Transforming Growth Factor–β1" *Dev. Biol.* 152:354–362 (1992).

Sporn et al., "Polypeptide Transforming Growth Factors Isolated from Bovine Sources and Used for Wound Healing in vivo" *Science* 219:1329–1331 (1983).

Van Obberghen–Schilling et al., "Transforming Growth Factor β1 Positively Regulates Its Own Expression in Normal and Transformed Cells" *J. Biol. Chem.* 263:7741–7746 (1988).

Wang et al., "Expression Cloning and Characterization of the TGF–β Type III Receptor" *Cell* 67:797–805 (1991).

Yamaguchi et al., "Negative regulation of transforming growth factor–β by the proteoglycan decorin" *Nature* 346:281–284 (1990).

Massague, "Identification of Receptors for Type–β Transforming Growth Factor" *Meth. Enzymol.* 146:174–195 (1987).

Edwards et al., "Transforming growth factor beta modulates the expression of collagenase and methalloproteinase inhibitor" *EMBO J.* 6:1899–1904 (1987).

Kulkarni et al., "Transforming growth factor β1 null mutation in mice causes excessive inflammatory response and early death" *PNAS USA* 90:770–774 (1993).

Cheifetz, S., et al. (1991) *J. Biol. Chem.* 266:20767–72.

Bützow, R., et al. (1993) *J. Cell Biochem.* 122:721–27.

Scopes, R. (1982) *Protein Purification,* New York: Springer–Verlag.

Jakoby, W. B., ed. (1984) *Meth. Enzymol.,* v. 104, *Enzyme Purification and Related Techniques.*

60 KDA TRANSFORMING GROWTH FACTOR-β-BINDING PROTEIN AND ITS USE TO DETECT OR PURIFY TGF-β

This invention was made with government support under CA42507, CA28896 and CA30199 awarded by The National Cancer Institute. The government has certain rights in the invention.

Throughout this disclosure, various publications are referred to within parentheses. Full bibliographic citations for these references is found immediately preceding the claims. The disclosures of the references are incorporated by reference herein.

BACKGROUND OF THE INVENTION

TGF-βs play an important role in the regulation of cell proliferation and in tissue repair (for reviews see Roberts and Sporn, 1990; Massagué, 1990). The TGF-β family consists of three known isoforms, TGF-β1, 2, and 3, that are structurally and functionally closely related to one another.

TGF-β is a potent growth suppressor for epithelial, myeloid, and lymphoid cells. This together with the observation that many transformed cells are resistant to the growth suppressing effects of TGF-β suggests that TGF-β functions as a general homeostatic factor suppressing undesired cell proliferation. Consequently, abnormalities in TGF-β function have been implicated in cellular transformation and malignancy (Masui et al., 1986; Shipley et al., 1986; Knabbe et al., 1987) and in a lymphoproliferative disorder seen in mice lacking a functioning TGF-β1 gene (Shull et al., 1992; Kulkarni et al., 1993). A prominent feature among TGF-β activities is the ability of this growth factor to enhance the deposition of extracellular matrix and stabilize such matrices (Sporn et al., 1983; Roberts et al., 1986). This is accomplished by increased production of extracellular matrix proteins (Balza et al., 1988; Ignotz and Massagué, 1986; Bassols and Massagué, 1988; Pearson et al., 1988) and their cellular receptors (Ignotz and Massagué, 1987) as well as decreased proteolysis (Edwards et al., 1987; Laiho et al., 1987). These activities of TGF-β are important in tissue repair.

TGF-β induces its own production in many cells (Van Obberghen-Schilling et al., 1988; Kim et al., 1989), and sometimes this self-amplifying cascade can lead to excessive and destructive fibrous tissue formation (Border and Ruoslahti, 1992). The fact that TGF-β is the driving force in many fibrotic disorders is suggested by elevated TGF-β expression at the site of excessive matrix formation and by the ability of neutralizing anti-TGF-β antibodies to hinder the development and progression of such disorders (Border and Ruoslahti, 1992). Considering the potency of TGF-β in eliciting both beneficial and potentially harmful responses, an effective regulatory system balancing TGF-β activity would be desirable.

One of the regulators of TGF-β activity is the binding of TGF-β to cell surface components other than signal transducing receptors and to extracellular matrices (Ruoslahti and Yamaguchi, 1991). A cell surface proteoglycan, betaglycan (also known as TGF-β receptor type III), binds TGF-β at the cell surface (Massagué, 1992) apparently enhancing the binding of TGF-β to one of the signal transducing receptors (Wang et al., 1991). A number of extracellular matrix (ECM) components have also been shown to bind TGF-β. These include fibronectin (Fava and McClure, 1987), thrombospondin (Murphy-Ullrich et al., 1992), collagen type IV (Paralkar et al., 1991) and the core proteins of small interstitial glycans of the decorin family (Yamaguchi et al., 1990). The binding of TGF-β to the decorin-type proteoglycans neutralizes the activity of the growth factor (Yamaguchi et al., 1990; Border et al., 1992). While betaglycan and the decorin-type proteoglycans bind TGF-β through the core protein, TGF-β can also bind to glycosaminoglycan chains of proteoglycans (McCaffrey et al., 1992). Immunohistochemical stainings have shown that, indeed, TGF-β can be found in the extracellular matrix in vivo (Flanders et al., 1989; Heine et al., 1990; Silberstein et al., 1992), but the binding proteins involved in this localization are not known. This invention provides a purified TGF-β binding protein.

SUMMARY OF THE INVENTION

This invention provides a novel purified TGF-β binding protein, alone or complexed with TGF-β. The TGF-β binding protein is useful to purify TGF-β in a sample and to modify the regulatory activities of TGF-β.

BRIEF DESCRIPTION OF THE FIGURES

FIG. 4A shows the autoradiograms of the fixed and dried gels scanned to quantitate the amount of the labeled 60-kD protein. The exposure time of the autoradiograms was 24 hours for the NaCl eluates and 3 days for the Triton X-100 extracts. In the graph shown in FIG. 4B, each absorbance was multiplied by three to adjust for the difference in exposure times. (● NaCl; (o) Triton.

DETAILED DESCRIPTION OF THE INVENTION

Figures 1A, 1B:
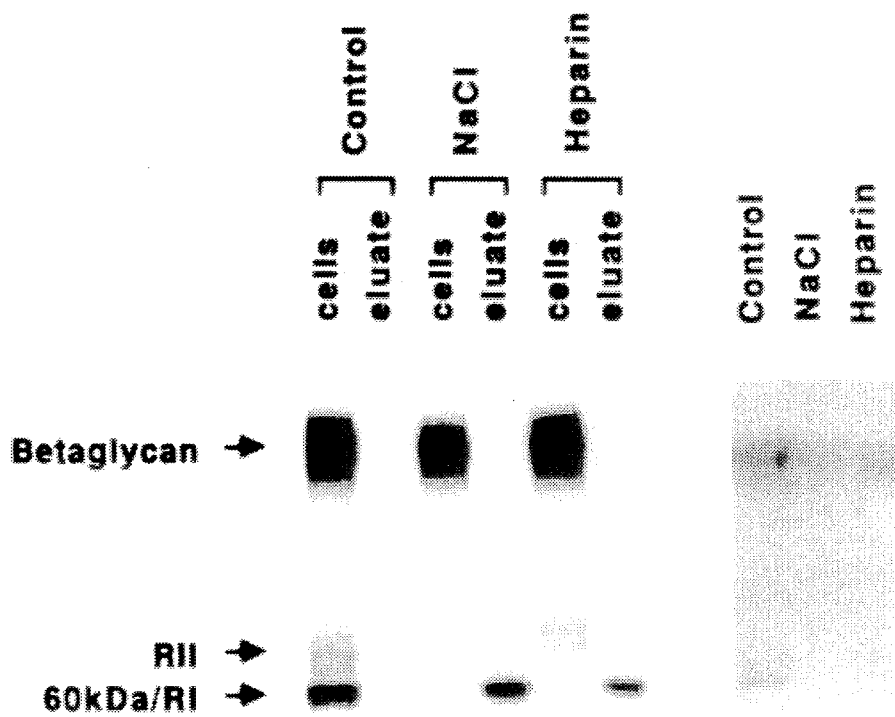
FIGS. 1A and 1B show the identification of 60-kD TGF-β1 binding protein. Briefly, HEP-G2 cells on 6-well dishes were affinity-labeled using 200 pM of $^{125}$I-TGF-β1. The cultures were incubated with 0.5 ml buffer (binding buffer with 200 µg/ml β-lactoglobulin as a carrier) with or without 1M NaCl or 10 µg/ml heparin for 15 min. The proteins in the eluates were TCA-precipitated and washed with acetone. The salt-extracted cultures were then further extracted with buffer containing 1% Triton X-100, and the eluates and the Triton extracts were analyzed by SDS-PAGE followed by autoradiography (See FIG. 1A). The Triton X-100-insoluble material containing ECM proteins was solubilized with 8M urea and 5×SDS-PAGE sample buffer and analyzed as above (See FIG. 1B).

The biological activity of many cytokines is regulated by binding proteins present at the cell surface, in extracellular matrices or in soluble phase. Described herein is a TGF-β binding protein that is both an extracellular matrix and a cell surface protein. When intact extracellular matrices of HEP-G2 cells were affinity cross-linked with $^{125}$I-TGF-β1, two major binding components were seen: a 250-kD, proteoglycan-like molecule, presumed to be betaglycan, and a 60-kD protein. The 60-kD TGF-β-binding protein was also present at the cell surface. It could be released from the cell surface by treating cells with high salt, heparin, chondroitin sulfate, heparitinase, or chondroitinase, indicating that it is bound to heparan sulfate and chondroitin sulfate proteoglycans. The 60-kD protein bound TGF-β1 with an apparent dissociation constant of 1.6 nM, and there were 30,000 binding sites per cell at the cell surface. In addition to the HEP-G2 cells and another hepatoma cell line, the 60-kD protein was also found in a human colon carcinoma (HT-29) cell line but not in rat kidney (NRK-49F) or human fibroblast (HUT-12) cell lines. The 60-kD protein can be extracted or purified from cells containing it and transferred to the surface of previously negative cells. The 60-kD protein can serve to regulate the binding of TGF-β to its signal transducing receptors by targeting TGF-β to appropriate locations in the microenvironment of cells.

This invention provides a purified TGF-β binding protein or "binding protein" having an apparent molecular mass of about 50 kD to about 70 kD on SDS-PAGE under reducing conditions. In one embodiment, the protein has an apparent molecular mass of about 60 kD on SDS-PAGE under reducing conditions. The protein can be purified from suitable mammalian cells; for example, human colon carcinoma cells and human hepatoma cells.

As used herein, the term "purified" means that the binding protein is substantially free of contaminants normally associated with a native or natural environment. In its natural or native environment, the binding protein of this invention is both an extracellular and a cell surface protein. Methods of purifying the protein are described in detail below.

Also encompassed by this invention are biologically active fragments of the binding protein. An "active fragment" or "biologically active fragment" is any portion of the binding protein that can bind TGF-β. Methods of determining whether a polypeptide can bind TGF-β are well known to those of skill in the art, for example as explained below. Indeed, any utility asserted for the binding protein is equally applicable to a "biologically active fragment."

The invention also encompasses nucleic acid molecules which encode the binding protein. As used herein, the term "nucleic acid" encompasses RNA as well as single and double-stranded DNA and cDNA. In addition, as used herein, the term "polypeptide" or "protein" encompasses any naturally occurring allelic variant thereof as well as man-made recombinant forms.

This invention provides an isolated nucleic acid molecule encoding a TGF-β binding protein or active fragment thereof. As used herein, the term "isolated nucleic acid molecule" means a nucleic acid molecule that is in a form that does not occur in nature. One means of isolating a TGF-β binding protein nucleic acid is to probe a human cDNA expression library with a natural or artificially designed antibody to binding protein, using methods well known in the art (see Gougos, A. et al., J. Biol Chem., 265:8361 (1990)). DNA and cDNA molecules which encode TGF-β binding protein can be used to obtain complementary genomic DNA, cDNA or RNA from human, mammalian or other animal sources.

The invention further provides the isolated nucleic acid molecule opertively linked to a promoter of RNA transcription, as well as other regulatory sequences. As used herein, the term "operatively linked" means positioned in such a manner that the promoter will direct the transcription of RNA off of the nucleic acid molecule. Examples of such promoters are SP6, T4 and T7. Vectors which contain both a promoter and a cloning site into which an inserted piece of DNA is operatively linked to that promoter are well known in the art. Preferable, these vectors are capable of transcribing RNA in vitro or in vivo. Examples of such vectors are the pGEM series (Promega Biotec, Madison, Wis.).

This invention provides a vector comprising this isolated nucleic acid molecule such as DNA, cDNA or RNA encoding a TGF-β binding protein. Examples of vectors are viruses, such as bacteriophages, baculoviruses and retroviruses, cosmids, plasmids (such as pcEXV-2) and other recombination vectors. Nucleic acid molecules are inserted into vector genomes by methods well known in the art (Sambrook et al., (1989)). For example, insert and vector DNA can both be exposed to a restriction enzyme to create complementary ends on both molecules that base pair with each other and which are then joined together with a ligase. Alternatively, synthetic nucleic acid linkers can be ligated to the insert DNA that correspond to a restriction site in the vector DNA, which is then digested with a restriction enzyme that recognizes a particular nucleotide sequence. Additionally, an oligonucleotide containing a termination codon and an appropriate restriction site can be ligated for insertion into a vector containing, for example, some or all of the following: a selectable marker gene, such as neomycin gene for selection of stable or transient transfectants in mammalian cells; enhancer/promoter sequences from the immediate early gene of human CMV for high levels of transcription; transcription termination and RNA processing signals from SV40 for mRNA stability; SV40 polyoma origins of replication and ColE1 for proper episomal replication; versatile multiple cloning sites; and T7 and SP6 RNA promoters for in vitro transcription of sense and anti-sense RNA. Other means are available.

Also provided are vectors comprising a DNA molecule encoding TGF-β binding protein or active fragment thereof, adapted for expression in a bacterial cell, a yeast cell, a mammalian cell and other animal cells. The vectors additionally comprise the regulatory elements necessary for expression of the DNA in the bacterial, yeast, mammalian or animal cells so located relative to the DNA encoding binding protein or fragment as to permit expression thereof. Regulatory elements required for expression include promoter sequences to bind RNA polymerase and transcription initiation sequences for ribosome binding. For example, a bacterial expression vector includes a promoter such as the lac promoter and for transcription initiation the Shine-Dalgarno sequence and the start codon AUG (Sambrook et al. supra. 1989). Similarly, a eucaryotic expression vector includes a heterologous or homologous promoter for RNA polymerase II, a downstream polyadenylation signal, the start codon AUG, and a termination codon for detachment of the ribosome. Such vectors can be obtained commercially or assembled by the sequences described in methods well known in the art, for example the methods described above for constructing vectors in general. Expression vectors are useful to produce cells that will express the protein.

This invention provides a mammalian cell containing a cDNA molecule encoding TGF-β binding protein or a fragment thereof. An example is a mammalian cell comprising a plasmid adapted for expression in a mammalian cell. The plasmid has a cDNA molecule encoding a binding protein or fragment and the regulatory elements necessary for expression of the polypeptide. Various mammalian cells may be utilized as hosts, including, for example, mouse fibroblast cell, Hep-G2, Hep-3B, and HT-29 cells. Expression plasmids such as those described supra can be used to tranfect mammalian cells by methods well known in the art such as calcium phosphate precipitation, DEAE-dextran, electropotation or microinjection.

The purified or recombinantly produced binding proteins or fragments thereof are useful to detect levels of TGF-β in a sample suspected of containing TGF-β. A sample is a cell or tissue sample obtained from a mammal, e.g., human, mouse, or rat. The binding protein or fragments can be used for the production of anti-TGF-β binding protein antibodies. The binding proteins and fragments also are useful to purify TGF-β from a sample as described in more detail below.

Also provided by this invention is a purified TGF-β complex ("binding complex") having an apparent molecular mass of about 65 kD to about 80 kD on SDS-PAGE under reducing conditions. In one embodiment, the molecular mass of the complex is about 72 kD on SDS-PAGE under reducing conditions.

This invention further provides a pharmaceutical composition containing a pharmaceutical carrier and any of a purified binding protein, an active fragment thereof, a purified binding complex, or an anti-binding protein antibody or fragment thereof, alone or in combination with each other. These polypeptides or proteins can be recombinantly derived, chemically synthesized or purified from native sources. As used herein, the term "pharmaceutically acceptable carrier" encompasses any of the standard pharmaceutical carriers, such as a phosphate buffered saline solution, water and emulsions such as an oil/water or water/oil emulsion, and various types of wetting agents.

Also provided by this invention is a method of modifying the activity of TGF-β in a tissue or cell by contacting the target tissue or cell with an effective amount of the binding protein. Also encompassed by this invention are polypeptides that retain their activity to bind to TGF-β, but no longer mediate the biological response corresponding to the binding of TGF-β to its receptor. Thus, these "mutated" polypeptides can act as antagonists to the biological function mediated by TGF-β by blocking the binding of normal, functioning TGF-β to its receptor on the cell.

Antibodies raised against binding protein or a fragment thereof also are useful in the practice of this method. Methods of generating such antibodies are well known to those of skill in the art. In one embodiment, the antibody is a monoclonal antibody, e.g., a human monoclonal antibody or a murine monoclonal antibody.

An effective amount is any amount that is effective to inhibit or increase the activity of TGF-β, whichever is desired. The method can be practiced in vitro or in vivo. If the method is practiced in vitro, contacting is effected by incubating the antibody or binding protein with the cell or tissue sample.

However, in a preferred embodiment the contacting is effected in vivo by administering the antibody or binding protein to a subject, e.g., a rat, mouse or a human patient. Methods of administration are well known to those of skill in the art and include, but are not limited to administration orally, intravenously or parenterally. Administration will be in such a dosage such that the activity of TGF-β is effectively increased or inhibited. Administration can be effected continuously or intermittently such that this amount is effective for its intended purpose.

Also provided are antibodies having specific reactivity with the TGF-β-binding protein. Active fragments of antibodies are encompassed within the definition of "antibody." The antibodies of the invention can be produced by any method known in the art. For example, polyclonal and monoclonal antibodies can be produced by methods well known in the art, as described, for example, in Harlow and Lane, *Antibodies: A Laboratory Manual* (Cold Spring Harbor Laboratory 1988), which is incorporated herein by reference. The protein can be used as the immunogen in generating such antibodies. Altered antibodies, such as chimeric, humanized, CDR-grafted or bifunctional antibodies can also be produced by methods well known to those skilled in the art. Such antibodies can also be produced by hybridoma, chemical synthesis or recombinant methods described, for example, in Sambrook et al., supra. (1989). The antibodies can be used for determining the presence or purification of the binding protein.

Immunological procedures useful for in vitro detection of the binding protein in a sample include immunoassays that employ a detectable antibody. Such immunoassays include, for example, ELISA, Pandex microfluorimetric assay, agglutination assays, flow cytometry, serum diagnostic assays and immunohistochemical staining procedures which are well known in the art. An antibody can be made detectable by various means well known in the art. For example, a detectable marker can be directly or indirectly attached to the antibody. Useful markers include, for example, radionuclides, enzymes, fluorogens, chromogens and chemiluminescent labels.

This invention provides a method of modifying a biological function mediated by the regulatory activity of TGF-β which comprises contacting a suitable sample containing TGF-β with an effective amount of the binding protein or fragment or an anti-binding protein antibody. Addition of binding protein can increase binding of TGF-β to its regulatory signal while addition of antibody can decrease binding of TGF-β to its regulatory signal. Examples of regulatory activities include, but are not limited to stimulation of cell proliferation, cell growth inhibition, or promotion of extracellular matrix proteins.

An effective amount is any amount that is effective to modify the biological function mediated by the regulatory activity of TGF-β. The method can be practiced in vitro or in vivo. If the method is practiced in vitro, contacting is effected by incubating the sample with a polypeptide, a protein or a pharmaceutical composition as described above.

However, in a preferred embodiment the contacting is effected in vivo by administering a polypeptide, a protein or a pharmaceutical composition, as described above, to a subject, e.g., a human patient.

Methods of administration are well known to those of skill in the art and include, but are not limited to administration orally, intravenously or parenterally. Administration will be in such a dosage such that the regulatory activity is effectively modified. Administration can be effected continuously or intermittently such that this amount is effective for its intended purpose.

This invention also provides a method of treating a pathologic condition caused by a TGF-β-regulated activity comprising contacting the TGF-β with any of a binding protein, an active fragment thereof, an anti-TGF-β binding protein antibody or an active fragment thereof. The binding protein is bound with the anti-binding protein antibody or TGF-β to thereby treat the pathologic condition mediated by TGF-β regulatory activity. As used herein, "pathologic conditions" refers to any pathology arising from TGF-β-induced regulatory activity. For example, growth and proliferation of mesenchymal cells is stimulated by TGF-β, however some tumor cells may also be stimulated thus using TGF-β as an autocrine growth factor. An example of inhibitory conditions are the prevention of new cell growth to assist in repair of tissue damage. The stimulation of extracellular matrix production by TGF-β is essential for wound healing. However, in some cases, the TGF-β response is uncontrolled and an excessive accumulation of extracellular matrix results. An example of excessive accumulation of extracellular matrix is glomerulonephritis. Additional examples of pathologies include cancer, rheumatoid arthritis and atherosclerosis.

In a preferred embodiment, the method is practiced by administering to a subject, e.g., a human patient, an effective amount of the binding protein, active fragment thereof or antibody or fragment thereof. Methods of administration are outlined supra.

A method of detecting the presence of TGF-β in a sample also are provided. The method includes obtaining a sample suspected of containing TGF-β, contacting the sample with detectably labeled binding protein under conditions favoring the binding of TGF-β to the TGF-β binding protein, and detecting the presence of any TGF-β binding protein bound to TGF-β, presence of which indicates TGF-β in the sample.

A method for purifying TGF-β from a sample is further provided. The method requires contacting the sample with an immobilized matrix, the matrix having accessibly bound TGF-β binding protein, under conditions favoring formation of binding protein to TGF-β to form a complex, removing TGF-β binding protein from the complex, removing the TGF-β from the immobilized matrix by treating the complex with an effective amount of a releasing buffer to uncomplex the TGF-β binding protein and collecting the uncomplexed TGF-β. In a separate embodiment, the releasing buffer comprises concentrated NaCl or heparin.

It is understood that modifications which do not substantially affect the activity of the various molecules of this invention are also included within the definition of said molecules.

The following examples are intended to illustrate but not limit the present invention.

EXPERIMENTAL DETAILS

Materials

Hep-G2, Hep-3B, HT-29, and NRK-49F cells were obtained from American Type Culture Collection (HB 8065, HB 8064, HTB 38, CRL 1570, respectively). HUT-12 cells were kindly provided by Dr. J. Leavitt (Leavitt et al., 1987). FCS was purchased from Tissue Culture Biologicals (Tulare, Calif.) and L-glutamine and antibiotics from Irvine Scientific (Santa Ana, Calif.). DME was from GIBCO BRL (Gaithersburg, Md.), carrier-free Na$^{125}$I from Dupont-NEN (Burbank, Calif.). IODO-GEN was disuccinimidyl suberate from Pierce (Rockford, Ill.). SDS-PAGE precast gels were from Novex (San Diego, Calif.). Molecular weight standards came from GIBCO BRL and Centricon micro-concentrator from Amicon (Danvers, Mass.). V$_8$ protease (EC 3.4.21.19. *Staphylococcus aureus* endoproteinase Glu-C) was from Boehringer Mannheim Corp. (Indianapolis, Ind.). Vydac 218TP54 column (4.6×250 mm) was from Vydac Separations Group (Hesperia, Calif.). All other chromatographic materials including pre-packed PD-10 columns were from Pharmacia (Uppsala, Sweden). Heparitinase I and chondroitinase ABC were from Seikagaku (Tokyo, Japan). Other chemicals came from Sigma Immunochemicals (St. Louis, Mo.).

Cell Cultures

Cells were grown at 37° C. in a humidified 10% CO$_2$ in air atmosphere in DME containing 10% FCS. 10 mM L-glutamine, 100 IU/ml penicillin and 100 μg/ml streptomycin. Confluent cultures were detached by treatment for 5 minutes with PBS containing 0.2 mg of EDTA and 0.5 mg of trypsin per ml and replated at least 18 hours before the start of each experiment.

TGF-β1

TGF-β1 was expressed in CHO cells and purified as described earlier (Gentry et al., 1987). Before use, the purity of each stock was verified by reversed-phase HPLC on a Vydac 218TP54 column. The sample was dissolved in 0.06% trifluoroacetic acid (TFA) and injected into the column equilibrated with 0.06% TFA. A linear gradient of acetonitrile (0–60%) containing 0.06% TFA was used to elute the protein. Iodination of TGF-β1 was done using Iodo-Gen according to the manufacturer's instructions. The specific activity of the label ranged from 80 to 150 µCi/µg.

Ligand Binding and Affinity Labeling

Confluent monolayers of cells were used for affinity labeling experiments. The conditions used were essentially as described earlier (Massagué, 1987). The following buffers were used: 25 mM Hepes, pH 7.4, 125 mM NaCl, 5 mM $MgSO_4$, 5 mM KCl, 1 mM $CaCl_2$, 2 mg/ml BSA ("binding buffer"), 10 mM Tris-HCl, pH 7.4, 150 mM NaCl, 1% Triton X-100 ("solubilization buffer"), 10 µg/ml antipain, 10 µg/ml leupeptin, 2 mM benzamidine, 1 mM EDTA ("protease inhibitor cocktail," final concentrations). A fresh stock of disuccinimidyl suberate (DSS) (10 mg/ml in DMSO) was prepared for each experiment and a 1:200 dilution in binding buffer without BSA was used in cross-linking for 15 minutes on ice. The reaction was quenched by 10 mM Tris-HCl, pH 7.4, 150 mM NaCl and the samples were treated as indicated.

Electrophoresis, Autoradiography, and Densitometric Scanning

SDS-PAGE was performed according to Laemmli (1970). For autoradiography the gels were fixed after electrophoresis in 10% isopropanol. 10% acetic acid for 15 minutes and dried. Kodak X-O-MAT/AR film (Eastman Kodak Co., Rochester, N.Y.) with a Dupont Cronex enhancing screen was used for autoradiography. Densitometric scans of the autoradiograms were performed on a laser densitometer (Ultroscan XL, LKB 222-020).

Peptide Maps

To obtain peptide maps of the 60-kD TGF-β binding protein and the type I TGF-β receptor (TGF-β1RI), a large petri dish of HEP-G2 cells was affinity labeled with 400 pM of $^{125}$I-TGF-β. The 60-kD TGF-β1 binding protein was released by eluting the culture with 1M NaCl in binding buffer containing 200 µg/ml β-lactoglobulin as a carrier. The proteins in the eluate were precipitated with 10% TCA, acetone washed and solubilized to 8M urea, TBS, pH 7.4. To obtain TGF-β1RI after the NaCl extraction, the cells were washed three times with ice cold binding buffer without BSA, scraped off and extracted with solubilization buffer. The NaCl and Triton X-100 extracts were separated on a 4–12% SDS-PAGE gel under reducing conditions. Proteins labeled with $^{125}$I-TGF-β1 were electroeluted from gel segments with Centrilutor (Amicon) using Centricon 30-kD cutoff microconcentrators and 50% Laemmli running buffer containing 0.025% SDS. The proteins were precipitated with 10% TCA and $V_8$ protease digestion was done as described (Stone et al., 1990). After digestion the samples were analyzed on a 18% gel under reducing conditions, fixed, dried, and autoradiographed.

Affinity Measurements

Various concentrations of $^{125}$I-TGF-β1 alone (from 10 to 300 pM) or a fixed concentration of $^{125}$I-TGF-β1 (300 pM) and various concentrations of unlabeled TGF-β1 (total TGF-β1 concentration from 1 nM to 100 nM) was added to HEP-3B cultures on 24-well dishes. After a 3-hour incubation, washes, and cross-linking, the cultures were extracted with solubilization buffer supplemented with protease inhibitor cocktail, and the soluble material was analyzed by SDS-PAGE on a 4–20% gel under nonreducing conditions. The autoradiograph of the fixed and dried gel was scanned along each lane. Based on the known quantity of total counts loaded per lane and the relative intensity of individual bands in autoradiogram scans, the amount of bound and free ligand at various TGF-β1 concentrations was determined. Cross-linking efficiency was 20% and the apparent amount of bound ligand was multiplied by a factor of five to take this fact in to account. The cross-linking efficiency was assessed by determining the percentage of TGF-β that migrated as a dimer in SDS-PAGE under reducing conditions. The saturation curve and Scatchard analysis were done with the LIGAND-program (National Institutes of Health) using the data points obtained with TGF-β1 concentrations from 300 pM to 100 nM.

Treatment of Cells with Glycosaminoglycan-degrading Enzymes

Hep-3B cells were washed three times with Ham F12/DME (vol/vol 1:1, 37° C.) medium containing 0.2% BSA. Heparitinase I and chondroitinase ABC were added to the cultures in the above buffer at a concentration of 0.02 U/ml and incubated for 90 minutes at 37° C. The cells were washed three times with binding buffer before affinity labeling.

RESULTS

Identification of the 60-kD Binding Protein as a Peripheral Membrane and ECM Protein.

Figure 2:
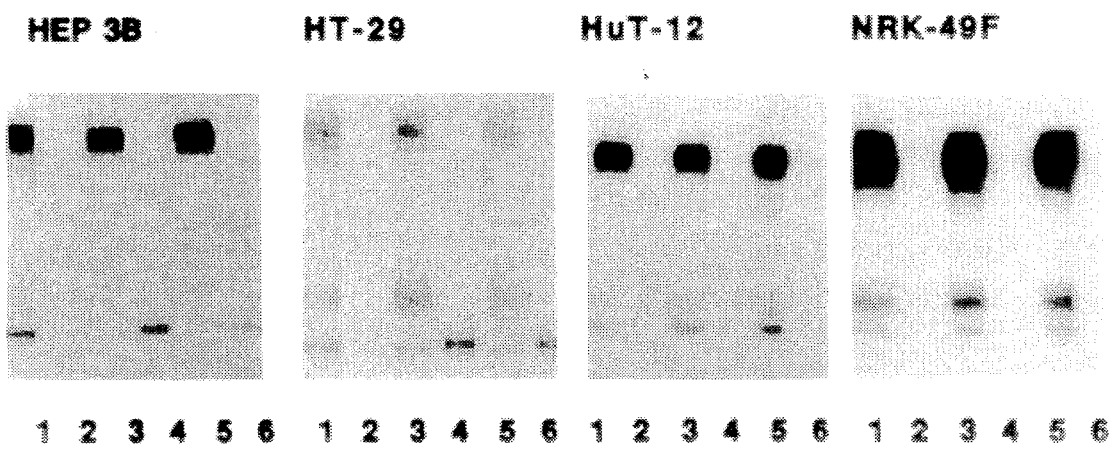
FIG. 2 shows the presence of 60-kD TGF-β1 binding protein in some but not all cell lines. HUT-12, NRK-49F, HEP-3B, and HT-29 cells on 6-well dishes were treated as described above. Buffer control, lanes 1 and 2; 1M NaCl treatment, lanes 3 and 4; heparin treatment, lanes 5 and 6. Cell extracts, lanes 1, 3, and 5; eluates, lanes 2, 4, and 6.

Affinity labeling of cultured HEP-G2 cells with $^{125}$I-TGF-β revealed three apparent cell surface-binding proteins with relative sizes of 72, 95, and 280 kD in a Triton X-100 extract of the cell layer (FIG. 1A). The sizes of these components correspond to type I and II receptors of TGF-β and betaglycan, respectively. A surprising finding was that much of what appeared to be the TGF-β-labeled 72-kD complex, presumably corresponding to the type I receptor, could be released from the cells and the matrix by treating the cultures with high salt and heparin after the affinity labeling. These results show that the 72-kD band may consist of two components: type I receptor (TGF-β1RI), which remains bound to the cell layer upon the heparin and salt treatments, and another TGF-β binding protein that is released by these treatments. Subtracting the molecular weight of the TGF-β subunit from the 72-kD size of the band indicates that the salt-released protein has a molecular mass of 60-kD. The Triton-insoluble material, consisting mainly of ECM, was solubilized with urea/SDS and also analyzed. The results show that the 72-kD complex and a proteoglycan slightly smaller than betaglycan were present in this material (FIG. 1B). The proteoglycan component could either be a truncated form of betaglycan or another TGF-β-binding proteoglycan, biglycan, which is SDS-PAGE migrates above 200 kD (Fisher et al., 1987). Analysis of other cell lines showed that the 72-kD complex was also present in heparin and salt extracts of affinity-labeled HEP-3B and HT-29 human colon carcinoma cells, but the HUT-12 human fibroblasts and NRK-49F rat kidney cells, judging from the absence of salt-extractable 72-kD complex, did not have detectable amounts of 60-kD protein (FIG. 2).

TGF-β1RI and 60-kD Binding Protein Are Distinct Proteins

Figure 3:
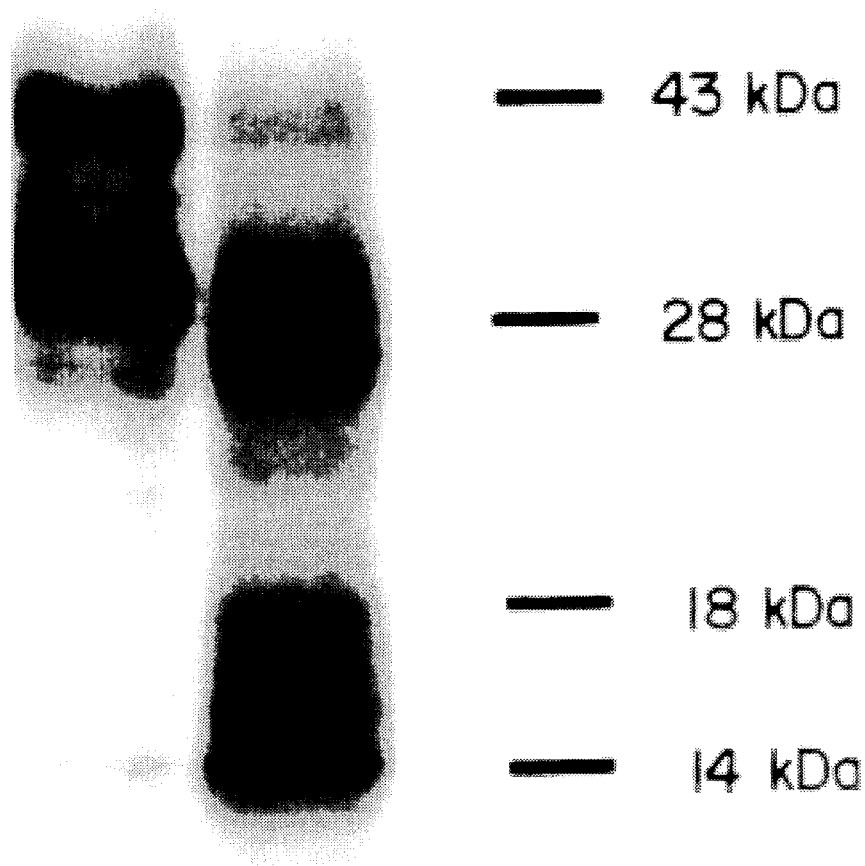
FIG. 3 is the peptide profiles of 60-kD TGF-β1 binding protein and TGF-β1RI. HEP-G2 cells were affinity-labeled with 500 pM of $^{125}$I-TGF-β1. The 60-kD TGF-β1 binding protein was eluted with 1M NaCl and the cells were solubilized. The samples were separated on SDS-PAGE under reducing conditions; the 60-kD protein and TGF-β1RI were electroeluted from the gel, alkylated, digested with V$_8$ protease, and the resulting fragments were separated on SDS-PAGE with an 18% gel. Lane 1, 60-kD protein; lane 2, TGF-β1RI.

Affinity labeled 60-kD binding protein and TGF-β1RI were analyzed by proteolytic cleavage to examine whether they are structurally related. While two fragments from both proteins appeared to migrate similarly, both proteins also yielded several fragments that were not present in the digest of the other protein (FIG. 3), indicating that the 60-kD protein and TGF-β1RI are two different proteins.

Figure 4A:
FIGS. 4A and 4B show the results of elution of 60-kD TGF-β1 binding protein from HEP-3B cells by increasing concentrations of NaCl. Briefly, HEP-3B cells on 6-well dishes were affinity labeled with 500 pM of $^{125}$I-TGF-β1. The cell layers were eluted with increasing concentrations of NaCl and the eluates and cells were processed as described in the description of FIG. 1. Aliquots from NaCl and Triton extracts were separated by 4–12% SDS-PAGE under reducing conditions.
Figure 4B:
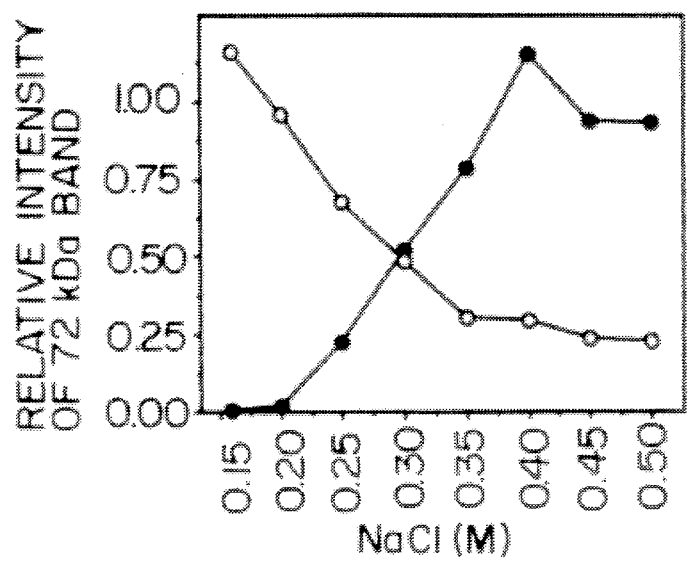

Release of 60-kD TGF-β1 Binding Protein from the Cell Surface at Various NaCl Concentrations When a stepwise gradient of NaCl was used to elute $^{125}$I-TGF-β1/60-kD binding protein complex from HEP-3B cultures after affinity labeling, little dissociation was observed with NaCl concentrations up to 0.20M (FIG. 4). Half-maximal and maximal elution were obtained by NaCl concentrations of 0.33 and 0.50M, respectively. There was an inverse relationship between the amount of $^{125}$I-TGF-β1/60-kD protein in the NaCl-eluate and the amount detected in the Triton X-100 extracts of the NaCl-treated cell layer. A 72-kD band was also observed in the Triton X-100 residue solubilized with urea/SDS. In cultures not treated with NaCl before the Triton extraction, the relative intensity of the 72-kD band present in the urea/SDS fraction representing extracellular matrix proteins was about half of that found in the Triton extract, indicating that a significant amount of the 72-kD complex was bound to the matrix.

Affinity of the 60-kD Binding Protein for $^{125}$I-TGF-β1

Figure 5A:
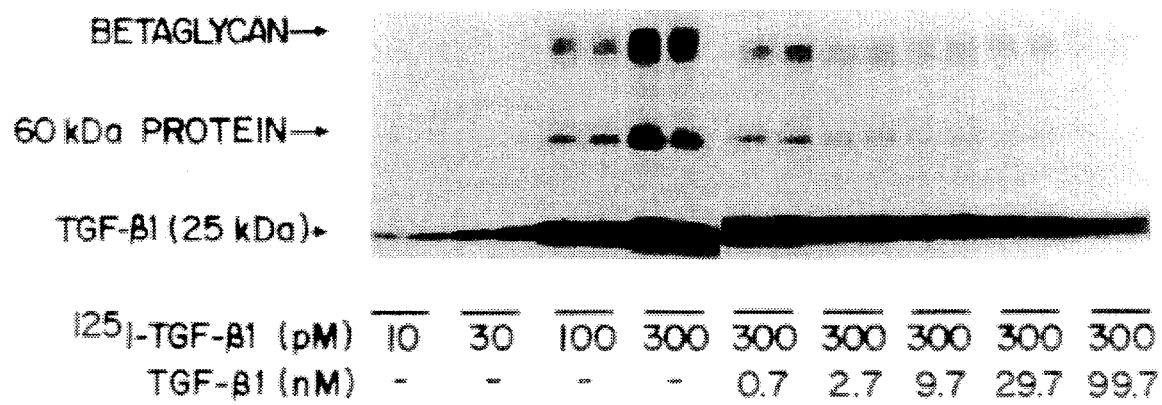
FIGS. 5A and 5B show affinity of 60-kD protein for TGF-β1. HEP-3B cells in duplicate wells of 24-well dishes were incubated for 3 hours at 4° C. with various concentrations of $^{125}$I-TGF-β1 (from 10 to 300 pM) or with a fixed concentration of $^{125}$I-TGF-β1 (300 pM) and various concentrations of unlabeled TGF-β1 (total TGF-β1 from 1 to 100 nM). After cross-linking, the cells were solubilized and extracts were analyzed by 4–20% SDS-PAGE under nonreducing conditions (See FIG. 5A). The gel bands were quantitated by scanning and the results plotted and shown in FIG. 5B. The inset shows a Scatchard plot generated from the results.
Figure 5B:
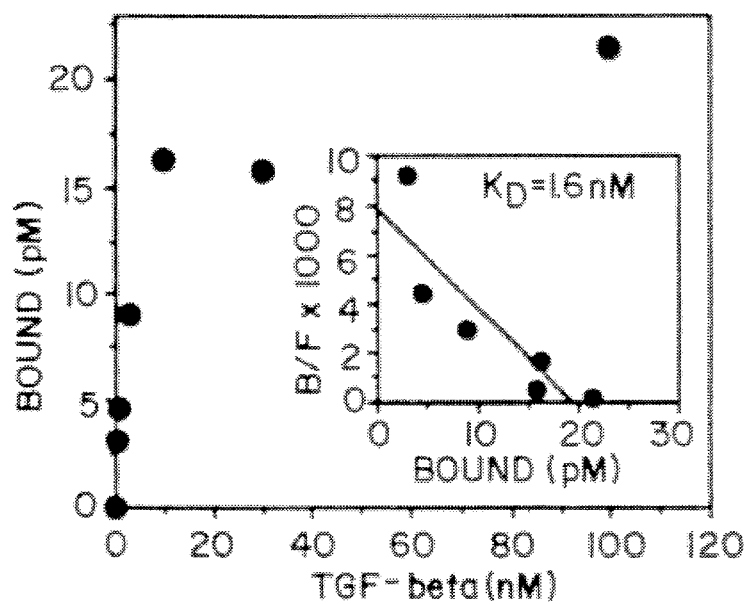

To determine the affinity of the 60-kD protein for TGF-β1, HEP-3B cells were incubated in the presence of various concentrations of TGF-β1, and the quantity of free TGF-β1 and that bound to the 60-kD component was determined. In Scatchard analysis of the data, the six highest data points were used to minimize the interference of the binding of TGF-β to the small amount of TGF-β1RI that comigrated with the TGF-β labeled 60-kD protein. As shown in FIG. 5, the binding of TGF-β1 to the 60-kD protein in these cells was saturable, and Scatchard analysis gave a rectilinear plot indicating a single class of binding sites with a $K_d$ of 1.6 nM. The number of binding sites was 30,000 per cell.

The 60-kD Protein Binds to Glycosaminoglycans

Figure 6:
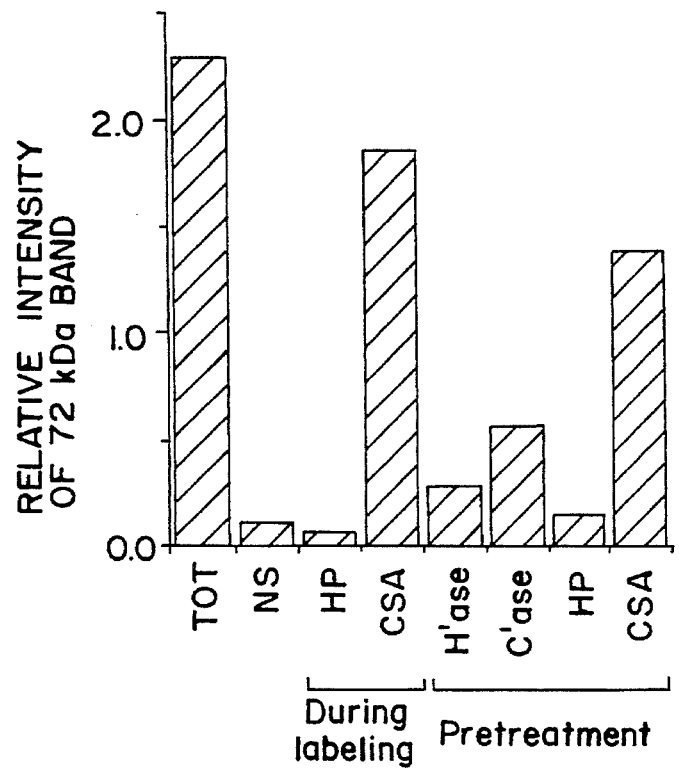
FIG. 6 graphically depicts the results of experiments to determine binding of 60-kD protein to glycosaminoglycans on Hep-3B cells. Hep-3B cells were digested with heparitinase (H'ase) or chondroitinase ABC (C'ase) as described in Materials and Methods or pretreated with heparin (HP: 100 µg/ml) or chondroitin sulfate A (CSA: 100 µg/ml) and washed three times with the binding buffer before affinity labeling of the cells with 200 pM of $^{125}$I-TGF-β1. Affinity labeling was done also in the presence of 100 µg/ml of heparin or chondroitin sulfate A. The relative intensity of $^{125}$I-TGF-β1-labeled 60-kD protein was quantified by scanning after SDS-PAGE and autoradiography.

The release of the 60-kD protein from the cell layers by high salt treatments suggested that the 60-kD protein may bind to glycosaminoglycan moieties on cell surface and in the ECM. To study this question, HEP-3B cells were treated with heparitinase or chondroitinase to eliminate potential binding sites for the 60-kD protein or with heparin and chondroitin sulfate as competitors for those sites. Subsequent affinity labeling with TGF-β showed that each of these treatments reduced the labeling of the 60-kD component (FIG. 6). Heparitinase was more effective than chondroitinase and heparin was more effective than chondroitin sulfate in reducing the amount of 60-kD protein detected on the cell surface.

Origin of 60-kD TGF-β Binding Protein

Figure 7:
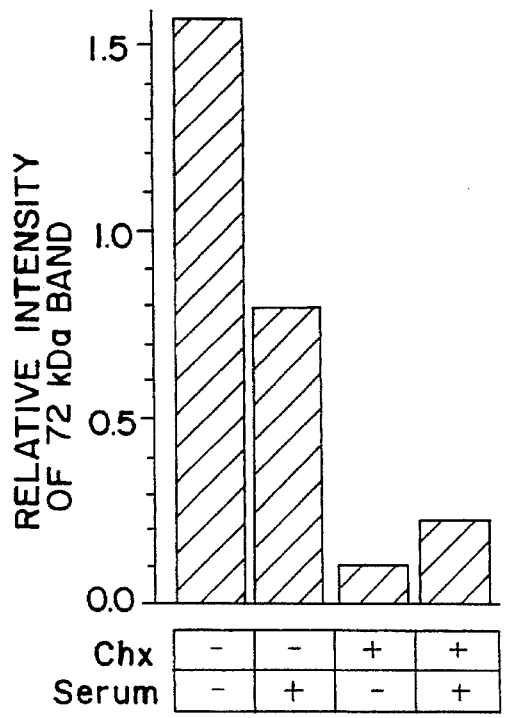
FIG. 7 shows the effect of serum and cycloheximide on 60-kD protein labeling at the cell surface. HEP-3B cells on 6-well dishes were incubated for 18 hours in the presence or absence of 10% FCS and/or 20 mM cycloheximide before affinity labeling with 500 pM of $^{125}$I-TGF-β-1. The cells were detached, solubilized and analyzed by SDS-PAGE on a 4–20% gel under reducing conditions. The relative intensity of the 72-kD band representing the 60-kD protein-TGF-β complex was quantitated by scanning (these cells have almost no detectable TGF-β1RI; see FIG. 2). The bars represent mean of duplicate experiments.

To determine whether the 60-kD protein originated from the cells or the serum present in the culture medium, HEP-3B cell cultures were incubated in the presence or absence of cycloheximide and/or 10% FCS. Addition of serum into the cultures decreased the 72-kD labeling to ~50% relative to the serum-free control (FIG. 7). Cycloheximide caused greatly diminished labeling of the 72-kD band both in serum-free and serum-containing cultures. Thus, the 60-kD binding protein does not originate from the serum but is synthesized by the cells and has a relatively short half-life on the cell surface.

Transfer of the 60-kD Protein from Producer to Nonproducer Cells

Figure 8:
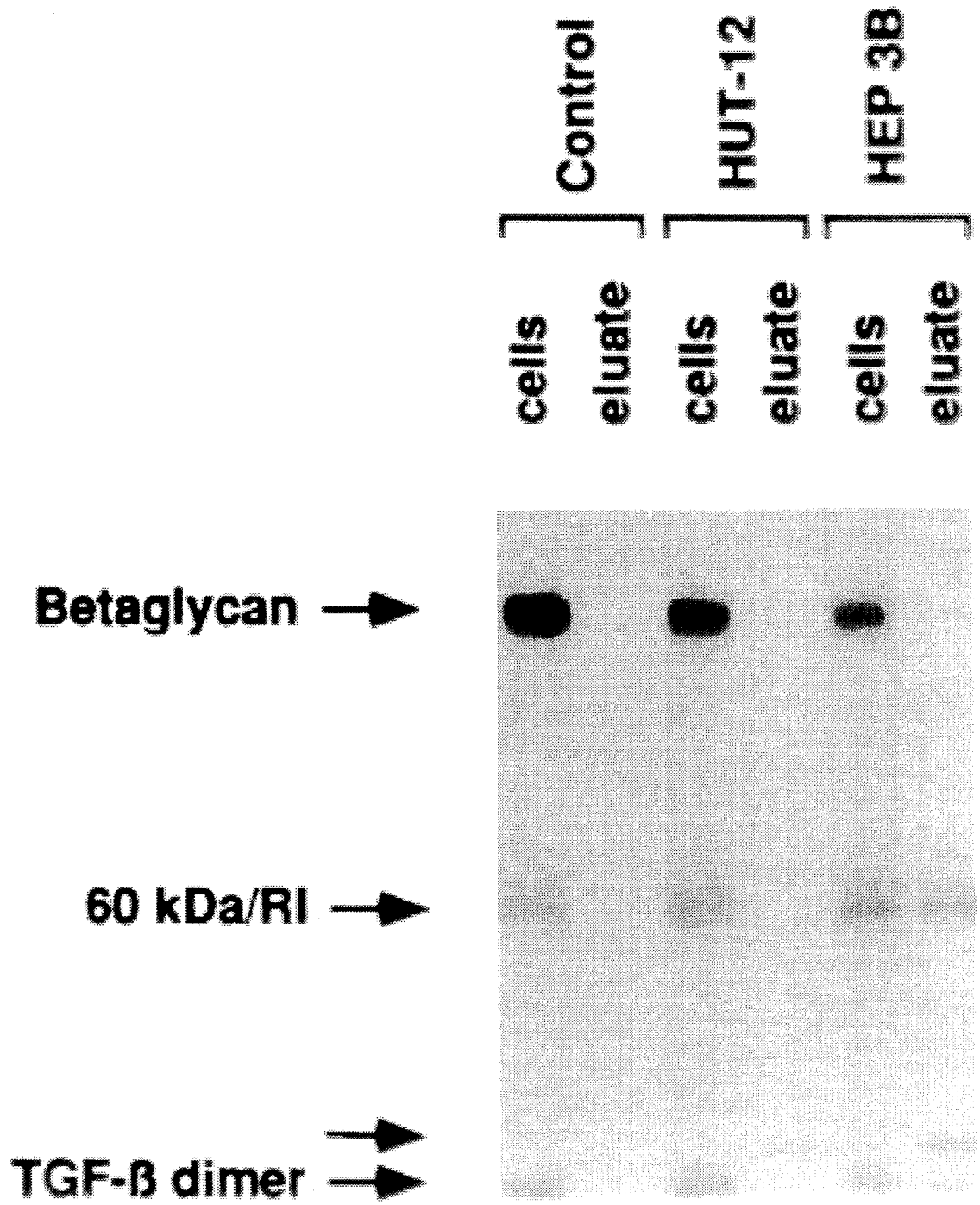
FIG. 8 shows the results of experiments regarding transfer of 60-kD TGF-β binding protein from cells producing it to non-producer cells. High salt extracts were prepared from confluent monolayer cultures of HEP-3B (60-kD protein-positive) and HUT-12 cells (60-kD protein-negative) grown on 140-mm petri dishes by incubating the cell layers with 0.5M NaCl in DMF containing 1% FCS for 10 minutes. The extracts were diluted with 25 mM Hepes, pH 7.4, containing 10% FCS to give physiological salt concentration and added, along with control media, to HUT-12 cells on 6-well dishes for 4 hours at 37° C. After three washes, the cultures were affinity-labeled using 300 pM of $^{125}$I-TGF-β1. The cultures were eluted with heparin (10 µg/ml), and treated and analyzed by SDS-PAGE as described in the legend of FIG. 1. The cells analyzed in the lanes labeled HUT-12 received the high salt extract from HUT-12 cells, and the lanes labeled HEP-3B received the extract from HEP-3B cells. Control indicates the cells treated with media only.

Whether it would be possible to extract the 60-kD binding component from 60-kD positive cells (HEP-3B) cells and transfer it to 60-kD negative (HUT-12) cells was examined. Treatment of HEP-3B cultures with salt produced an extract that when incubated with HUT-12 cells rendered these cells positive for the 72-kD, heparin-elutable component (FIG. 8).

DISCUSSION

This invention provides one of the cell surface proteins that affinity cross-link to radioactive TGF-β is a 60-kD peripheral membrane protein, and that this protein is bound to cell surfaces and ECMs through an interaction with the glycosaminoglycan component of proteoglycans. Since the 60-kD protein has a high affinity for both TGF-β and glycosaminoglycans, its function is to modulate the availability of TGF-β to cells likely by binding TGF-β to cell surfaces and to the ECM.

This 60-kD protein is similar to the TGF-β receptors in that it binds TGF-β specifically and with high affinity, but it has the novel property that it can be released from the cells by treatments that reverse protein-glycosaminoglycan interactions. The specificity of the labeling of the 60-kD protein with TGF-β is evident from the fact that the 60-kD protein is one of the few cell surface proteins that become affinity-labeled with TGF-β. Moreover, like the labeling of the known receptors, the labeling of the 60-kD with the $^{125}$I-TGF-β1 was inhibited by unlabeled TGF-β. The affinity constant of the 60-kD protein for the TGF-β1 was 1.6 nM, which is similar to the affinity measured for the type III receptor, betaglycan (1.9 nM; Andres et al., 1989).

The 60-kD protein migrates as a 72-kD protein after affinity labeling with TGF-β. The protein has not yet been identified without association with radiolabeled TGF-β and the designation of 60-kD as its molecular mass is based on the assumption that one 12-kD subunit of TGF-β remains associated with it when the affinity-labeled products are analyzed by gel electrophoresis under reducing conditions.

The TGF-β-labeled 60-kD protein essentially comigrates with the type I TGF-β receptor at 72 kD. However, it can be distinguished from the type I receptor, because the receptor behaves as a transmembrane protein (Massagué, 1985), whereas the 60-kD protein can be released from the cell surface by treatments that do not cleave polypeptide chains. Moreover, the peptide maps of the two proteins were different. The comigration of the 60-kD protein with the type I receptor under the affinity-labeling conditions customarily used in the analysis of TGF-β-binding, cell-surface proteins can explain why the 60-kD protein has been generally overlooked by prior investigators.

The 60-kD protein is not likely to be one of the other well-characterized TGF-β binding proteins. The proteins known to bind to TGF-β—fibronectin (Fava and McClure, 1987), thrombospondin (Murphy-Ullrich et al., 1992), type IV collagen (Paralkar et al., 1991), decorin (Yamaguchi et al., 1990), betaglycan (Andres et al., 1989), type II receptor (Lin et al., 1992) α$_2$-macroglobulin (O'Connor-McCourt and Wakefield, 1987), TGF-β-latency peptide (Miller et al., 1992), endoglin (Cheifetz et al., 1992), and the amyloid protein (Bodmer et al., 1990)— each have a size different from that of the 60-kD binding protein described here.

Another protein that may have a relationship to this 60-kD protein is follistatin (Vale et al., 1990), a 35-kD activin-biding protein that inhibits the binding of activin to its receptors. Follistatin is clearly not the same protein as the 60-kD protein, because follistatin does not bind TGF-β and the sizes of the two proteins (35-kD versus 60-kD) also differ. It is also unlikely that follistatin and the 60-kD protein would be homologues, because follistatin is rich in cysteine and shows marked changes in mobility in SDS-PAGE upon reduction, whereas the 60-kD protein lacks this feature.

Several lines of evidence in this study show that the TGF-β-complexed 60-kD protein is bound to cells through an interaction with the glycosaminoglycan moieties of proteoglycans. First, the binding of the 60-kD protein-TGF-β1 complex to cell layers can be reversed by treating the cells with high salt or with heparin; both of these treatments disrupt protein-glycosaminoglycan interactions. Since TGF-β can interact directly with heparin (McCaffrey et al., 1992), the results would leave open the possibility that the complex would be binding to the cellular glycosaminoglycans through its TGF-β component. However, the evidence presented here indicates that the 60-kD protein interacts directly with cellular glycosaminoglycans and heparin. Thus, treatment of cell layers with heparin or chondroitin sulfate before the TGF-β affinity labeling reduced the subsequent yield of the 60-kD protein-TGF-β complex, indicating that the glycosaminoglycans had released the 60-kD protein from its binding to cell layer glycosaminoglycans. That the 60-kD protein labeling could also be reduced by treating cell layers with glycosaminoglycan-degrading enzymes points to the same conclusion. These results also indicate that the 60-kD protein can bind to both heparan sulfate and chondroitin sulfate proteoglycans. Moreover, the weaker effect of chondroitin sulfate and chondroitinase suggested that, as is usual for protein-glycosaminoglycan interactions (Ruoslahti, 1988), chondroitin sulfate is a weaker binder of the 60-kD protein than heparan sulfate. Since TGF-β itself binds only weakly to heparin, the main force of the binding of the 60-kD protein-TGF-β complex to glycosaminoglycans is likely to be contributed by the 60-kD protein. However, it is likely the complex can bind even more strongly than the 60-kD protein alone.

The glycosaminoglycan binding of the 60-kD protein-TGF-β complex may direct the 60-kD protein and the TGF-β bound to it either to cell surfaces or to the ECM fraction in the cell cultures. The distribution of the complex in the detergent soluble (cell membrane) and insoluble (ECM) fractions was markedly different from that of betaglycan (Andres et al., 1989) of which only a minor fraction was in the ECM compartment. The 60-kD protein may, therefore, differ from the membrane protein betaglycan in that the 60-kD protein directs a higher portion of TGF-β bound to it to the ECM. This difference may be even more marked in tissues, which are likely to contain a more abundant ECM than the tumor cell cultures used in this study.

The 60-kD protein can serve as an effector in a negative feedback loop: increased TGF-β effect would lead to increased matrix formation (Bassols and Massagué, 1988; Border and Ruoslahti, 1992) and the increased content of decorin along with the matrix-increased binding of the 60-kD protein would then sequester TGF-β to the matrix. This matrix could act as a buffer for TGF-β activity; it would compete with the receptors but would at the same time constitute a potential reservoir for prolonged TGF-β activity and counteract the extremely short plasma half-life (3–5 min) of mature TGF-β.

REFERENCES

Andres et al., *J. Cell Biol.* 109:3137–3145 (1989)

Balza et al., *FEBS (Fed. Eur. Biochem. Soc.) Lett.* 228:42–44 (1988)

Bassols et al., *J. Biol. Chem.* 263:3039–3045 (1988)

Bodner et al., *Biochem. Biophys. Res. Commun.* 171:890–897 (1990)

Border et al., *J. Clin. Invest.* 90:1–7 (1992)

Border et al., *Nature (Lond.)* 360–361–363 (1992)

Cheifetz et al., *J. Biol. Chem.* 263:17225–17228 (1988)

Cheifetz et al., *J. Biol. Chem.* 267:19027–19030 (1992)

Edwards et al., *EMBO (Eur. Mol. Biol. Organ) J.* 6:1899–1904 (1987)

Fava et al., *J. Cell. Physiol.* 131:184–189 (1987)

Fisher et al., *J. Biol. Chem.* 262:9702–9708 (1987)

Flanders et al., *J. Cell. Biol.* 108:653–660 (1989)

Gentry et al., *Mol. Cell. Biol.* 7:3418–3427 (1987)

Heine et al., *Development (Camb.)* 109:29–36 (1990)

Ignotz et al., *J. Biol. Chem.* 261:4337–4345 (1986)

Ignotz et al., *Cell* 51:189–197 (1987)

Kim et al., *J. Biol. Chem.* 264:7041–7045 (1989)

Knabbe et al., *Cell* 48:417–428 (1987)

Kulkarni et al., *Proc. Natl. Acad. Sci. USA* 90: 770–774 (1993)

Laemmli, U.K., *Nature (Lond.)* 227:680–685 (1970)

Laiho et al., *J. Biol. Chem.* 262-17467–17474 (1987)

Leavitt et al., *Mol. Cell. Biol.* 7:2457–2466 (1987)

Lin et al., *Cell* 68:775–785 (1992)

Massagué, J., *J. Biol. Chem.* 260:7059–7066 (1985)

Massagué, J., *Methods. Enzymol.* 147:174–195 (1987)

Massagué, J., *Annu. Rev. Cell Biol.* 6:597–641 (1990)

Massagué, J., *Cell* 69:1067–1070 (1992)

Masui et al., *Proc. Natl. Acad. Sci. USA* 83: 2438–2442 (1986)

McCaffrey et al., *J. Cell Physiol.* 152:430–440 (1992)

Miller et al., *Mol. Endocrinol.* 6:694–702 (1992)

Murphy-Ullrich et al., *Mol. Biol. Cell.* 3:181–188 (1992)

Nakamura et al., *J. Biol. Chem.* 266:19432–19437 (1991)

O'Connor-McCourt et al., *J. Biol. Chem.* 262:14090–14099 (1987)

Paralkar et al., *Dev. Biol.* 143:303–308 (1991)

Pearson et al., *EMBO (Eur. Mol. Biol. Organ) J.* 7:2977–2981 (1988)

Roberts et al., *M. B. Sporn and A. B. Roberts (eds),*

Springer-Verlag/Heidelberg. 419–472 (1990)

Roberts et al., *Proc. Natl. Acad. Sci. USA* 83:4167–4171 (1986)

Ruoslahti, E., *Annu. Rev. Cell Biol.* 4:229–255 (1988)

Ruoslahti et al., *Cell* 64:867–869 (1991)

Sambrook et al., *Molecular Cloning: A Laboratory Manual*, Cold Spring Harbor Press (1989)

Shipley et al., *Cancer Res.* 46:2068–2071 (1986)

Shull et al., *Nature (Lond.)* 359:693–699 (1992)

Silberstein et al., *Dev. Biol.* 152:354–362 (1992)

Sporn et al., *Science (Wash. D.C.)* 219:1329–1330 (1983)

Stone et al., *In: A Practical Guide to Protein and Peptide Purification for Microsequencing.* P. T. Matsudaira (ed), Academic Press, Inc./San Diego, Calif. (1990)

Vale et al., *In: Handbook of Experimental Pharmacology, Peptide Growth Factors and Their Receptors*, M. B. Sporn and A. B. Roberts (eds), Springer-Verlag/Heidelberg 211–248 (1990)

Van Obberghen-Schilling et al., *J. Biol. Chem.* 263:7741–7746 (1988)

Wang et al., *Cell* 67:797–805 (1991)

Yamaguchi et al., *Nature (Lond.)* 346:281–284 (1990)

What is claimed is:

1. An isolated human protein which is capable of specifically binding to TGF-$\beta$1, said protein characterized in that it can be recovered from Hep-G2 or HT-29 cells as a soluble protein following elution from said cells with 0.5M NaCl, and in that a covalently cross-linked complex of said protein and a TGF-$\beta$ comigrates with a similarly cross-linked type I receptor for TGF-$\beta$ at about 72 kDa when a sample containing said protein and said type I receptor is resolved by SDS-PAGE under reducing conditions.

2. The protein of claim 1 which has been detectably labeled.

3. A method of determining whether a sample contains TGF-$\beta$, comprising the steps of:
   a) contacting the sample with detectably labeled TGF-$\beta$ binding protein of claim 2 under conditions favoring the binding of TGF-$\beta$ to said TGF-$\beta$ binding protein; and
   b) detecting the presence of any of said binding protein which is bound to TGF-$\beta$, the presence of which indicates that the sample contains TGF-$\beta$.

4. An affinity matrix having immobilized thereon the protein of claim 1, wherein said immobilized protein retains the ability to bind to TGF-$\beta$1.

5. A method for isolating TGF-$\beta$ from a sample, comprising the steps of:
   a) contacting the sample with the affinity matrix of claim 4 under conditions favoring the binding of TGF-$\beta$ to said TGF-$\beta$ binding protein;
   b) removing a complex comprising said TGF-$\beta$ binding protein and TGF-$\beta$ from the matrix;
   c) treating the complex of step b with an effective amount of a releasing buffer to dissociate the TGF-$\beta$ from said complex; and
   d) collecting the dissociated TGF-$\beta$.

* * * * *